United States Patent [19]

Seward

[11] Patent Number: 5,564,431

[45] Date of Patent: Oct. 15, 1996

[54] FLEXIBLE STETHOSCOPE COVER, COVER PACKAGE AND DISPENSING SYSTEM

[76] Inventor: Regina Seward, 91595 Pupu St., Ewa Beach, Hi. 96706

[21] Appl. No.: 340,523

[22] Filed: Nov. 16, 1994

[51] Int. Cl.⁶ .................................................. A61B 19/02
[52] U.S. Cl. ............................................ 128/715; 206/69
[58] Field of Search ................................... 128/715, 918, 128/DIG. 24; 181/131; 206/69; D24/134

[56] References Cited

U.S. PATENT DOCUMENTS

| | | | |
|---|---|---|---|
| 4,401,125 | 8/1983 | Taylor et al. | 128/715 |
| 4,867,268 | 9/1989 | Ulert | 181/131 |
| 4,871,046 | 10/1989 | Turner | D24/134 |
| 5,172,683 | 12/1992 | West | 181/131 |
| 5,269,314 | 12/1993 | Kendall et al. | 128/715 |
| 5,365,023 | 11/1994 | Lawton | 181/131 |
| 5,466,897 | 11/1995 | Ross et al. | 181/131 |

*Primary Examiner*—William E. Kamm
*Assistant Examiner*—Kennedy J. Schaetzle

[57] ABSTRACT

A stethoscope cover for enclosing the head of a stethoscope to preclude both temperature and germ transfer. The inventive device includes a pair of circular webs joined together by a side wall web. The webs are formed of a resilient material and are stored in a rolled condition, whereby the device can be installed to the stethoscope head by unrolling the cover over the head. The inventive device also includes a disposable package for containing the cover, as well as a container for its dispensal.

11 Claims, 3 Drawing Sheets

FLEXIBLE STETHOSCOPE COVER, COVER PACKAGE AND DISPENSING SYSTEM

BACKGROUND OF THE INVENTION

1. Field of the Invention

The present invention relates to covering structures and more particularly pertains to a flexible stethoscope cover for enclosing the head of a stethoscope to preclude both temperature and germ transfer.

2. Description of the Prior Art

The use of covering structures is known in the prior art. More specifically, covering structures heretofore devised and utilized are known to consist basically of familiar, expected and obvious structural configurations, notwithstanding the myriad of designs encompassed by the crowded prior art which have been developed for the fulfillment of countless objectives and requirements.

Known prior art covering structures include U.S. Pat. Nos. 4,871,046; 5,269,314; 4,461,368; 4,401,125; 4,867,265.

While these devices fulfill their respective, particular objectives and requirements, the aforementioned patents do not disclose a stethoscope cover for enclosing the head of a stethoscope to preclude both temperature and germ transfer which includes a pair of circular webs joined together by a side wall web, wherein the webs are formed of a resilient material and are stored in a rolled condition such that the device can be installed to the stethoscope head by unrolling the cover over the head.

In these respects, the flexible stethoscope cover according to the present invention substantially departs from the conventional concepts and designs of the prior art, and in so doing provides an apparatus primarily developed for the purpose of enclosing the head of a stethoscope to preclude both temperature and germ transfer.

SUMMARY OF THE INVENTION

In view of the foregoing disadvantages inherent in the known types of covering structures now present in the prior art, the present invention provides a new flexible stethoscope cover construction wherein the same can be utilized for enclosing the head of a stethoscope to preclude both temperature and germ transfer. As such, the general purpose of the present invention, which will be described subsequently in greater detail, is to provide a new flexible stethoscope cover apparatus and method which has many of the advantages of the covering structures mentioned heretofore and many novel features that result in a flexible stethoscope cover which is not anticipated, rendered obvious, suggested, or even implied by any of the prior art covering structures, either alone or in any combination thereof.

To attain this, the present invention generally comprises a stethoscope cover for enclosing the head of a stethoscope to preclude both temperature and germ transfer. The inventive device includes a pair of circular webs joined together by a side wall web. The webs are formed of a resilient material and are stored in a rolled condition, whereby the device can be installed to the stethoscope head by unrolling the cover over the head.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new flexible stethoscope cover apparatus and method which has many of the advantages of the covering structures mentioned heretofore and many novel features that result in a flexible stethoscope cover which is not anticipated, rendered obvious, suggested, or even implied by any of the prior art covering structures, either alone or in any combination thereof.

It is another object of the present invention to provide a new flexible stethoscope cover which may be easily and efficiently manufactured and marketed.

It is a further object of the present invention to provide a new flexible stethoscope cover which is of a durable and reliable construction.

An even further object of the present invention is to provide a new flexible stethoscope cover which is susceptible of a low cost of manufacture with regard to both materials and labor, and which accordingly is then susceptible of low prices of sale to the consuming public, thereby making such flexible stethoscope covers economically available to the buying public.

Still yet another object of the present invention is to provide a new flexible stethoscope cover which provides in the apparatuses and methods of the prior art some of the advantages thereof, while simultaneously overcoming some of the disadvantages normally associated therewith.

Still another object of the present invention is to provide a new flexible stethoscope cover for enclosing the head of a stethoscope to preclude both temperature and germ transfer.

Yet another object of the present invention is to provide a new flexible stethoscope cover which includes a pair of circular webs joined together by a side wall web, wherein the webs are formed of a resilient material and are stored in a rolled condition such that the device can be installed to the stethoscope head by unrolling the cover over the head.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
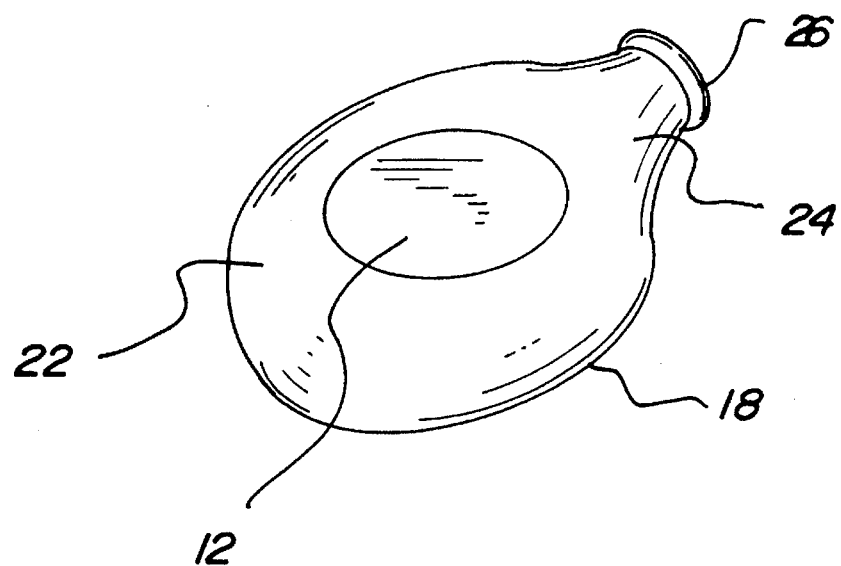
FIG. 1 is an isometric illustration of a flexible stethoscope cover according to the present invention.

With reference now to the drawings, and in particular to FIGS. 1–6 thereof, a new flexible stethoscope cover embodying the principles and concepts of the present invention and generally designated by the reference numeral 10 will be described.

Figure 2:
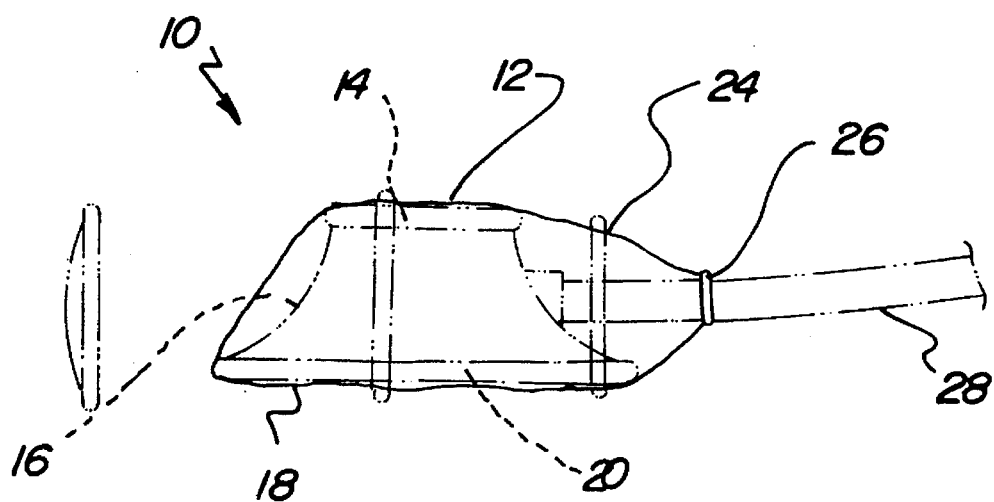
FIG. 2 is a side elevation view of the flexible stethoscope cover as installed upon a stethoscope head.

More specifically, it will be noted that the flexible stethoscope cover 10 comprises a first circular web 12 having a first diameter sufficient to coextensively cover the top portion 14 of a stethoscope head 16, as best illustrated in FIGS. 1 and 2. The device 10 further includes a second circular web 18 of a second diameter sufficient to coextensively cover the sound receiving surface 20 of the stethoscope head 16. In accordance with the design of a typical stethoscope head 16, the first diameter of the first circular web 12 will be substantially less than the second diameter of the second circular web 18. The circular webs 12, 18 are integrally coupled together by a side wall web 22 which extends between the outer circumferences of both the first circular web 12 and the second circular web 18. Further, the side wall web 22 continues into a tapered neck web 24 of a substantially conical tubular shape. The neck web 24 terminates in a resilient neck cuff 26 which sealingly extends about a sound tube 28 of the stethoscope when the cover 10 is installed over the stethoscope head 16, as shown in FIG. 2. Because the resilient neck cuff 26 sealingly engages the sound tube 28, the covered stethoscope head 16 can be immersed during a sterilization process or the like.

Preferably, the stethoscope cover 10 is rolled about the resilient neck cuff 26 for storage. As such, the resilient neck cuff 26 of the stethoscope cover 10 can then be stretched into the phantom illustration of FIG. 2, whereby a rolling of the resilient neck cuff over the stethoscope head 16 allows the cover to be applied substantially as shown. Because of the resilient nature of the material used to construct the stethoscope cover 10, preferably a latex rubber or other similar material, the cover will resiliently encapsulate the stethoscope head 16 to cause the second circular web 18 to be drawn tightly against the sound receiving surface 20 such that interference of the sound being transferred to the sound receiving surface is substantially reduced.

Figure 3:
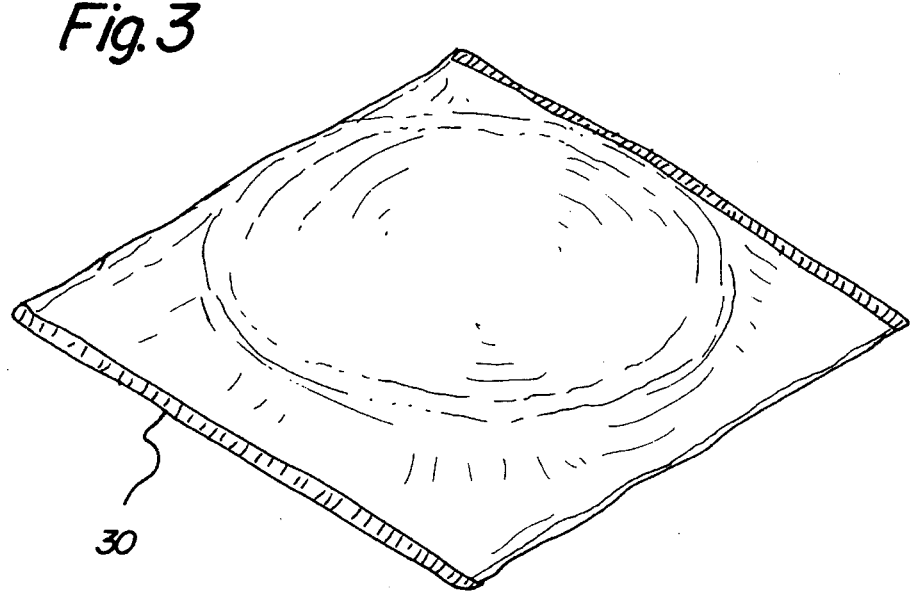
FIG. 3 is an isometric illustration of the invention contained within a disposable package.
Figure 4:
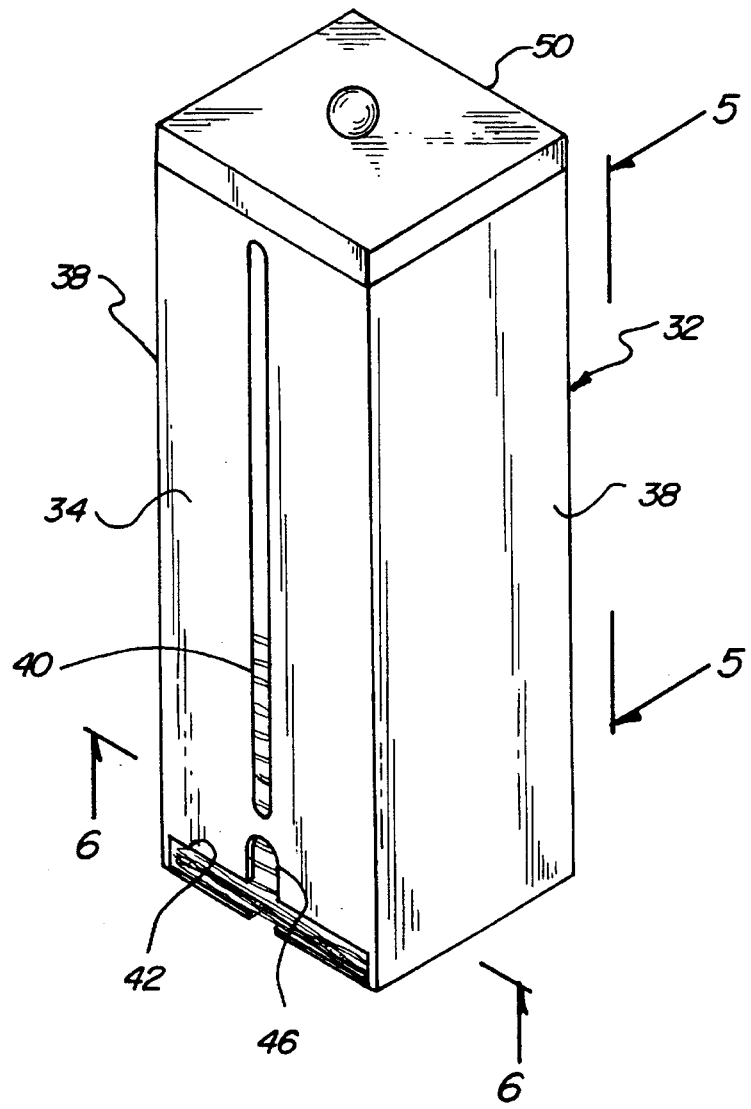
FIG. 4 is an isometric view of a dispensing container comprising a portion of the present invention.

Turning now to FIGS. 3 and 4, it can be shown that the stethoscope cover 10 is preferably enclosed within a disposable package 30 which may be selectively opened prior to use of the device 10, whereby such package maintains the freshness of the resilient material of the cover, and further provides for the maintenance of the sterile environment within which the cover can be stored. The disposable package 30 may be dispensed from a dispensing container 32 wherein a plurality of such covers 10, each within an individual disposable package 30, are stacked one on top of another within the dispensing container. To this end, the dispensing container 32 comprises a front wall 34 spaced from a rear wall 36, with the front wall being separated from the rear wall by a pair of side walls 38 which orthogonally extend between the front wall and the rear wall. The front wall 34 is provided with a vertical slot 40 directed therethrough which permits a user to visually ascertain a level or a number of the covers 10 stored within the dispensing container 32. Further, the front wall 34 includes a substantially rectangular package access hole 42 located at a lowermost end thereof through which an individual disposable package 30 may be pulled from the dispensing container 32, with the lowermost disposable package resting upon a bottom wall 44 orthogonally connected to the front wall 34, the rear wall 36 and both of the side walls 38.

To facilitate easier removal an individual one of the covers 10 from the dispensing container 32, the front wall 34 further includes an index finger access hole 46, and the bottom wall 44 includes a thumb access hole 48. By this arrangement, an individual desiring to remove a single one of the disposable packages 30 containing an individual cover 10 from the dispensing container 32 may simply direct his index finger between the lower most adjacent packages, whereby the individual's thumb may be engaged to the lowermost package through the thumb access hole 48 to grip the lowermost package, whereby such package may then be pulled through the package access hole 42 of the dispensing container 32. A lid 50 removably coupled to an upper most portion of the dispensing container 32 permits the addition of more covers 10 into the container as desired.

Figure 5:
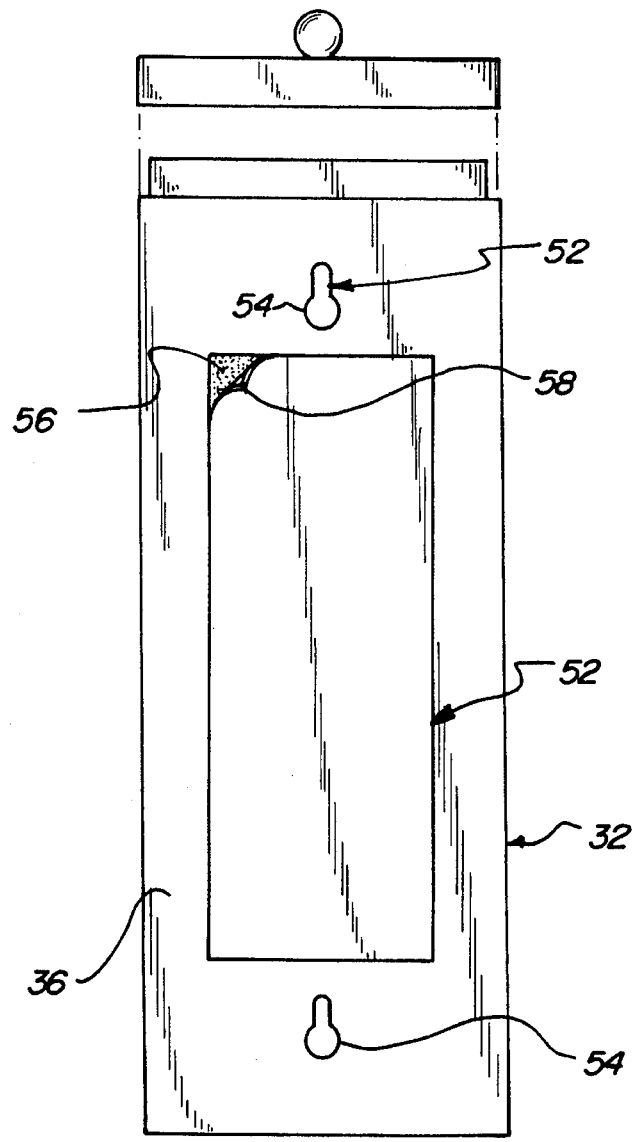
FIG. 5 is a rear elevation view of the dispensing container taken from line 5—5 of FIG. 4.
Figure 6:
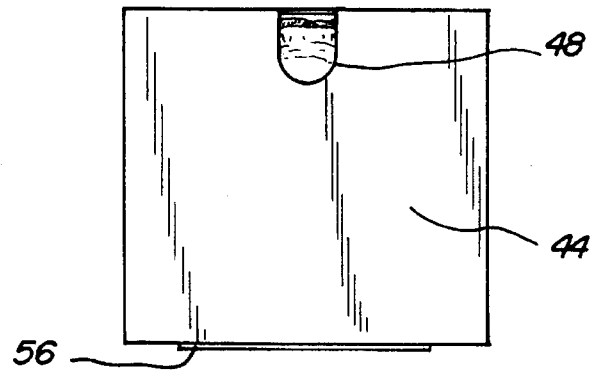
FIG. 6 is a bottom plan view of the dispensing container taken from line 6—6 of FIG. 4.

Turning now to FIGS. 5 and 6, the dispensing container 32 is shown as being provided with a mounting means 52 for selectively mounting the dispensing container to a vertical wall surface. To this end, the mounting means 52 may comprise either a pair of spaced slotted mounting holes 54, or alternatively, an adhesive pad 56 having a removable backing 58 secured to the rear wall 36 of the dispensing container 32.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A flexible stethoscope cover, package and dispenser comprising:

a first circular web having a first diameter for coextensively covering a top portion of a stethoscope head;

a second circular web of a second diameter for coextensively covering a sound receiving surface of said stethoscope head;

a side wall web extending between outer circumferences of both said first circular web and said second circular web, said side wall web continuing into a tapered neck web of a substantially conical tubular shape, with said neck web terminating in a resilient neck cuff; a packaging means for receiving and releasably containing said cover; and, a dispensing container means for dispensing a plurality of said covers.

2. The system of claim 1, wherein said first diameter of said first circular web is substantially less than said second diameter of said second circular web.

3. The system of claim 2, wherein said neck cuff is operable to sealingly extend about a sound tube of said stethoscope when said cover is installed over said stethoscope head, wherein said stethoscope head can be immersed.

4. The system of claim 3, wherein said cover is formed of a resilient material, wherein said second circular web is drawn tightly against said sound receiving surface of said stethoscope head such that interference of sound being transferred through said cover to the sound receiving surface is substantially reduced.

5. The system of claim 4, wherein said stethoscope cover is rolled about said resilient neck cuff for storage, wherein said resilient neck cuff of the stethoscope cover can be stretched to permit a rolling of said resilient neck cuff over said stethoscope head to install said stethoscope head within said cover.

6. The system of claim 5, wherein the packaging means is disposable.

7. The system of claim 6, wherein said dispensing container means comprises a dispensing container having a front wall spaced from a rear wall, a bottom wall, and a pair of side walls, said front wall having a vertical slot directed therethrough which permits a user to visually ascertain a number of covers stored within said dispensing container, said front wall further including a substantially rectangular package access hole located at a lowermost end thereof through which an individual disposable package can be pulled from the dispensing container, with a lowermost disposable package resting upon said bottom wall; and a mounting means for selectively mounting said dispensing container to a vertical wall surface.

8. The system of claim 7, wherein said front wall further includes an index finger access hole directed therethrough, and said bottom wall includes a thumb access hole directed therethrough such that an individual desiring to remove a single one of said disposable packaging means containing an individual cover from said dispensing container can direct his index finger between lowermost adjacent packaging means, whereby his thumb can be engaged to a lowermost packaging means through the thumb access hole to grip said lowermost packaging means, whereby said lowermost package can then be pulled through said package access hole of said dispensing container.

9. A flexible stethoscope cover, package and dispenser comprising:

a first circular web having a first diameter for coextensively covering a top portion of a stethoscope head, said first diameter of said first circular web being substantially less than said second diameter of said second circular web;

a second circular web of a second diameter for coextensively covering a sound receiving surface of said stethoscope head;

a side wall web extending between outer circumferences of both said first circular web and said second circular web, said side wall web continuing into a tapered neck web of a substantially conical tubular shape, with said neck web terminating in a resilient neck cuff, said neck cuff being operable to sealingly extend about a sound tube of said stethoscope when said cover is installed over said stethoscope head, said cover being integrally formed of a resilient material, such that said second circular web is drawn tightly against said sound receiving surface of said stethoscope head such that interference of sound being transferred through said cover to the sound receiving surface is substantially reduced, said stethoscope cover being rolled about said resilient neck cuff for storage, wherein said resilient neck cuff of the stethoscope cover can be stretched to permit a rolling of said resilient neck cuff over said stethoscope head to install said stethoscope head within said cover;

a disposable package for receiving and releasably containing said cover; and, a dispensing container means for dispensing a plurality of said covers, each of said covers being contained within a disposable package, said dispensing container means comprising a dispensing container having a front wall spaced from a rear wall, a bottom wall, and a pair of side walls, said front wall having a vertical slot directed therethrough which permits a user to visually ascertain a number of covers stored within said dispensing container, said front wall further including a substantially rectangular package access hole located at a lowermost end thereof through which an individual disposable package can be pulled from the dispensing container, with a lowermost disposable package resting upon said bottom wall; and a mounting means for selectively mounting said dispensing container to a vertical wall surface, said front wall further including an index finger access hole directed therethrough, and said bottom wall including a thumb access hole directed therethrough such that an individual desiring to remove a single one of said disposable packages containing an individual cover from said dispensing container can direct his index finger between lowermost adjacent packages, whereby his thumb can be engaged to a lowermost package through the thumb access hole to grip said lowermost package, whereby said lowermost package can then be pulled through said package access hole of said dispensing container; and a lid removably coupled to an uppermost portion of said dispensing container.

10. The system of claim 9, wherein said mounting means comprises a pair of spaced slotted mounting holes directed into said rear wall.

11. The system of claim 9, wherein said mounting means comprises an adhesive pad secured to said rear wall, said pad having a removable backing.

\* \* \* \* \*